US010269562B2

(12) United States Patent
Von Haenisch et al.

(10) Patent No.: US 10,269,562 B2
(45) Date of Patent: Apr. 23, 2019

(54) USE OF AT LEAST ONE BINARY GROUP 15 ELEMENT COMPOUND, A 13/15 SEMICONDUCTOR LAYER AND BINARY GROUP 15 ELEMENT COMPOUNDS

(71) Applicant: Philipps-Universität Marburg, Marburg (DE)

(72) Inventors: Carsten Von Haenisch, Linkenheim-Hochstetten (DE); Kerstin Volz, Dautphetal (DE); Wolfgang Stolz, Marburg (DE); Eduard Sterzer, Marburg (DE); Andreas Beyer, Marburg (DE); Dominik Keiper, Marburg (DE); Benjamin Ringler, Marburg (DE)

(73) Assignee: PHILIPPS-UNIVERSITÄT MARBURG, Marburg (DE)

( * ) Notice: Subject to any disclaimer, the term of this patent is extended or adjusted under 35 U.S.C. 154(b) by 0 days.

(21) Appl. No.: 15/511,911

(22) PCT Filed: Sep. 25, 2015

(86) PCT No.: PCT/EP2015/072163
§ 371 (c)(1),
(2) Date: Mar. 16, 2017

(87) PCT Pub. No.: WO2016/046394
PCT Pub. Date: Mar. 31, 2016

(65) Prior Publication Data
US 2017/0243740 A1    Aug. 24, 2017

(30) Foreign Application Priority Data
Sep. 26, 2014    (DE) .................. 10 2014 014 036

(51) Int. Cl.
| | |
|---|---|
| *H01L 21/02* | (2006.01) |
| *C07F 9/90* | (2006.01) |
| *C07F 9/46* | (2006.01) |
| *C07F 9/50* | (2006.01) |
| *C07F 9/72* | (2006.01) |
| *C23C 16/30* | (2006.01) |
| *C23C 16/22* | (2006.01) |

(52) U.S. Cl.
CPC .......... *H01L 21/02538* (2013.01); *C07F 9/46* (2013.01); *C07F 9/504* (2013.01); *C07F 9/72* (2013.01); *C07F 9/90* (2013.01); *C23C 16/22* (2013.01); *C23C 16/301* (2013.01); *H01L 21/0262* (2013.01); *H01L 21/0254* (2013.01); *H01L 21/02543* (2013.01); *H01L 21/02546* (2013.01); *H01L 21/02549* (2013.01)

(58) Field of Classification Search
None
See application file for complete search history.

(56) References Cited

U.S. PATENT DOCUMENTS

2014/0220733 A1* 8/2014 Hunks .................. C07C 251/08
                                                         438/102

FOREIGN PATENT DOCUMENTS

| FR | 2190830 A1 | 2/1974 |
| JP | H05-121340 A | 5/1993 |
| WO | 98/43988 A1 | 10/1998 |

OTHER PUBLICATIONS

Protzmann, H.et al. Properties of ($Ga_{0.47}In_{0.53}$) As epitaxial layers grown by metalorganic vapor phase epitaxy (MOVPE) using alternative arsenic precursors. Journal of Crystal Growth, No. 170, 1997, pp. 155-160.

Zimmermann, G. et al. GaAs substrate pretreatment and metalorganic vapour phase epitaxy of GaAs, AlAs and (AlGa)As using β-eliminating trialkyl-As precursors. Journal of Crystal Growth, 1994, No. 145, pp. 512-519.

Komeno, J. Metalorganic vapor phase epitaxy using organic group V precursors. Journal of Crystal Growth, 1994, No. 145, pp. 468-472.

Volz, K. et al. Specific structural and compositional properties of (GaIn)(NAs) and their influence on optoelectronic device performance. Journal of Crystal Growth, 2004, No. 272, pp. 739-747.

Volz, K. et al. MOVPE growth of dilute nitride III/V semiconductors using all liquid metalorganic precursors. Journal of Crystal Growth, 2009, No. 311, pp. 2418-2426.

Horita, M. et al. MOVPE growth of InGaAsP using TBA and TBP with extremely low V/III ratio. Journal of Crystal Growth, 1992, No. 124, pp. 123-128.

Scherer, O. et al. Elementorganische Amin/Imin-Verbindungen VII. Überführung Eines N-Silylierten Aminoarsins In Ein N-Silyl-Arsinimin. Journal of Organometallic Chemistry. 1969, No. 16, pp. 69-70.

(Continued)

*Primary Examiner* — Clinton A Brooks
*Assistant Examiner* — Kofi Adzamli
(74) *Attorney, Agent, or Firm* — Smith, Gambrell & Russell, LLP (57) ABSTRACT

The invention provides the use of at least one binary group 15 element compound of the general formula $R^1R^2E$-$E'R^3R^4$ (I) or $R^5E(E'R^6R^7)2$ (II) as the educt in a vapor deposition process. In this case, $R^1$, $R^2$, $R^3$ and $R^4$ are independently selected from the group consisting of H, an alkyl radical (C1-C10) and an aryl group, and E and E' are independently selected from the group consisting of N, P, As, Sb and Bi. This use excludes hydrazine and its derivatives. The binary group 15 element compounds according to the invention allow the realization of a reproducible production and/or deposition of multinary, homogeneous and ultrapure 13/15 semiconductors of a defined combination at relatively low process temperatures. This makes it possible to completely waive the use of an organically substituted nitrogen compound such as 1.1 dimethyl hydrazine as the nitrogen source, which drastically reduces nitrogen contaminations—compared to the 13/15 semiconductors and/or 13/15 semiconductor layers produced with the known production methods.

15 Claims, 1 Drawing Sheet

(56) References Cited

OTHER PUBLICATIONS

Scherer, O. et al. Metallorganische Aminophosphine und Phosphinimine. Chemische Berichte, 1968, vol. 101, No. 12, pp. 4184-4198.
Royen, P. et al. Darstellung gemischter flüchtiger Hydride des Phosphors, Arsens, Stickstoffs und Germaniums sowie von Triphosphin und Tnarsin. Angew. Chem. 1964, vol. 76, iss. 20, p. 860.
STREM Chemicals. MOCVD, CVD & ALD Precursors, Katalog 2014 (64 pages).
Kokorev, G. et al. Reaction of secondary Haloarsines with primary Amines. Properties and Structure of Bis(arsino)amines, Russ. J. Gen. Chem. 1992, pp. 1498-1501.
Cavell, R. et al. Preparation and Properties of Some Bis(trifluoromethyl)-phosphorus and -arsenic Derivatives containing P—P, P—As, and As—As Bonds. J. Chem. Soc. (A), 1968, pp. 1406-1410.
Kober, F. et al. Komplexe des Chroms, Molybdäns und Wolframs mit Aminoarsan-Liganden II. Z. Anorg. Allg. Chem. 1985, vol. 522, pp. 65-75.
Avens, L. et al. Some Perfluoralkyl-Substituted Tripnicogens and Their Hydrolysis to Yield Chiral Dipnicogens. Inorg. Chem. 1989, vol. 28, pp. 200-205.
International Preliminary Report on Patentability for PCT/EP2015/072163 dated Mar. 28, 2017 (6 pages).
International Search Report dated Feb. 2, 2016 for PCT/EP2015/072163 (5 pages).
Written Opinion of the International Search Authority for PCT/EP2015/072163 dated Feb. 2, 2016 (6 pages).

\* cited by examiner

USE OF AT LEAST ONE BINARY GROUP 15 ELEMENT COMPOUND, A 13/15 SEMICONDUCTOR LAYER AND BINARY GROUP 15 ELEMENT COMPOUNDS

The invention concerns the use of at least one binary group 15 element compound, a 13/15 semiconductor layer and binary group 15 element compounds.

13/15 semiconductors such as the binary compounds gallium arsenide (GaAs) or indium phosphide (InP) and the methods to produce them are known in the state of the art.

The representation of 13/15 semiconductors is usually achieved by deposition from the gas phase. Important production methods are, for instance, metal-organic chemical vapor deposition (MOCVD) and metal-organic vapor phase epitaxy (MOVPE). These methods allow the application of ultrapure layers of 13/15 semiconductor materials on a plurality of substrates. Such methods are, among other applications, used in the context of the production of light-emitting diodes, lasers, transistors and solar cells.

For example, for the representation of the binary 13/15 semiconductor GaAs, a gaseous mixture of the group 13 element precursor trimethylgallium ($Me_3Ga$) and the group 15 element precursor arsine ($AsH_3$) is disintegrated on a hot surface, depositing GaAs. The disintegration of the precursors is directly affected by the process temperature and the process pressure. Since precursors usually have relatively high disintegration temperatures, the process temperatures applied usually have to be high respectively. Other important process parameters are the concentration of the precursors, the concentration of the carrier gas and the reaction gas as well as the total gas flow.

In addition to binary 13/15 semiconductors such as GaAs, ternary 13/15 semiconductors such as nitrogenous gallium arsenide nitride ($GaAs_{1-x}N_x$) ($0<x<1$) as well quaternary and other multinary 13/15 semiconductors are important as these allow further variation and sensitive adjustments of opto-electronic characteristics than binary 13/15 semiconductors due to the presence of three or four different elements, namely of one or two group 13 elements and two or three group 15 elements.

The production of nitrogenous multinary 13/15 semiconductors, e.g. ternary $Ga(As_{1-x}N_x)$ ($0<x<1$), has so far been achieved by using three separate precursor compounds, namely one group 13 element source and two group 15 element sources. The three precursors are mixed during the gaseous phase and disintegrated together. This kind of representation of multinary 13/15 semiconductors does not only involve a high synthesis effort—especially due to the production of several precursor compounds—but also requires the consideration of different disintegration temperatures, vapor pressures and the respective different diffusion rates of the various precursors, e.g. three separate precursors for the production of the ternary compound $Ga(As_{1-x}N_x)$ ($0<X<1$). The method is furthermore not very atom-efficient.

Usually organically substituted nitrogen compounds are used, such as 1.1 dimethyl hydrazine. The disadvantage is that in addition to the desired inclusion of nitrogen there is also an undesired inclusion of carbon into the 13/15 semiconductors and/or the 13/15 semiconductor layers. Due to the carbon contamination, the opto-electronic characteristics of the 13/15 semiconductors and/or the 13/15 semiconductor layers are modified and/or impaired in an uncontrollable and irreversible way. Furthermore, the partial pressures usually required with regard to the nitrogen source are high. For example, if 1.1 dimethyl hydrazine is used as the nitrogen source, the two selected group 15 element sources, i.e. 1.1 dimethyl hydrazine and another group 15 element source must be present in a molar relationship to each other that is between 10:1 and 100:1. The nitrogen percentage thus achieved in the 13/15 semiconductor is, however, only 1-10% which negatively affects the efficiency of the method.

Examples and further details regarding vapor deposition of multinary 13/15 semiconductors on the basis of organically substituted group 15 element compounds such as $tBuAsH_2$, $tBu_2AsH$, $tBu_3As$, $Et_2tBuAs$, $Et_2iPrAs$, $tBu_3P$, $tBuPH_2$ are found in the respective literature, for example:

H. Protzmann, F. Höhnsdorf, Z. Spika, W. Stolz, E. O. Göbel, M. Müller, J. Lorberth, J. *Crystal Growth* 1997, 170, 155-160.

G. Zimmermann, Z. Spika, T. Marschner, B. Spill, W. Stolz, E. O. Göbel, P. Gimmnich, J. Lorberth, A. Greiling, A. Salzmann, *J. Crystal Growth* 1994, 145, 512-519.

J. Komeno, *J. Crystal Growth* 1994, 145, 468-472.

M. Horita, M. Suzuki, Y. Matsushima, *J. Crystal Growth* 1992, 124, 123-128.

K. Volz, J. Koch, F. Höhnsdorf, B. Kunert, W. Stolz, *J. Crystal Growth* 2009, 311, 2418-2426.

K. Volz, T. Torunski, B. Kunert, O. Rubel, S. Nau, S. Reinhard, VV. Stolz, *J. Crystal Growth* 2004, 272, 739-747.

The known process sequences to produce ternary 13/15 semiconductors must be regarded as rather inefficient in terms of use of energy and atom efficiency, and thus as on the whole rather uneconomical.

The invention therefore has the purpose to overcome these and other disadvantages in the state of the art and provide group 15 element compounds that are suitable for use as the educt in a process of vapor deposition, especially for the production of multinary 13/15 semiconductor compounds and/or layers.

The group 15 element compounds to be used should be characterized by the production of multinary, homogeneous and ultrapure 13/15 semiconductors and/or layers in a combination as defined that is as atom-efficient, cost-efficient and reproducible as possible. Furthermore, a 13/15 semiconductor layer should be provided that may be produced using group 15 element compounds as intended according to the invention. In addition, binary group 15 element compounds are to be provided.

The main characteristics of the invention are described herein together with a discussion of a variety of embodiments.

The purpose is achieved by the use of at least one binary group 15 element compound as the educt of a vapor deposition process, wherein the at least one binary group 15 element compound has the general formula of (I), wherein $R^1$, $R^2$, $R^3$ and $R^4$ are selected independently from one another from the group consisting of H, an alkyl radical (C1-C10) and an aryl group, and E and E' are selected independently from one another from the group consisting of N, P, As, Sb and Bi, wherein E=E' or E≠E', and/or wherein at least one binary group 15 element compound has the general formula (II), wherein $R^5$, $R^6$ and $R^7$ are selected independently from one another from the group consisting of H, an alkyl radical (C1-C10) and an aryl group, and E and E' are selected independently from one another from the group consisting of N, P, As, Sb and Bi, wherein E=E' or E≠E', The alkyl and/or aryl groups may be substituted, e.g. partly fluorinated or perfluorinated.

Specifically, $R^1$, $R^2$, $R^3$, $R^4$, $R^5$, $R^6$ and $R^7$ are the same or different and are selected from the group consisting of hydrogen (H), C1 to C6 alkyl radical and C1 to C8 aryl radical. In particular, $R^1$, $R^2$, $R^3$, $R^4$, $R^5$, $R^6$ and $R^7$ are the same or different and are selected from the group consisting of hydrogen (H), C1 to C4 alkyl radical and C1 to C6 aryl radical.

More specifically, $R^1$, $R^2$, $R^3$, $R^4$, $R^5$, $R^6$ and $R^7$ are the same or different and are selected from the group consisting of hydrogen (H), methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclobutyl, phenyl ($C_6H_5$) or ortho- meta- and para-toluyl.

The alkyl or aryl groups can be substituted, particularly fluorinated or perfluorinated. In this case, $R^1$, $R^2$, $R^3$, $R^4$, $R^5$, $R^6$ and $R^7$ may, in particular, be trifluormethyl ($CF_3$) or pentafluorphenyl ($C_6F_5$).

Most specifically, $R^1$, $R^2$, $R^3$, $R^4$, $R^5$, $R^6$ and $R^7$ are the same or different and are selected from the group consisting of hydrogen (H), methyl (Me), isopropyl (iPr), tert.-butyl (tBu or 2-methylpropyl). In a specific embodiment, E and E' are different and one of E or E' is N. In another specific embodiment of a compound of formula (I), $R^1$ and $R^2$ are hydrogen (H), if $R^3$ and $R^4$ are different from hydrogen, or $R^3$ and $R^4$ are hydrogen, if $R^1$ and $R^2$ are different from hydrogen.

In another embodiment, E and E' are selected from the group consisting of N, P, As and Sb. The invention does not concern the use of hydrazine ($H_2N$—$NH_2$) and its derivatives, especially 1.1 dimethyl hydrazine and tertiary butyl hydrazine as the educt in a vapor deposition process. These compounds are regarded as hydrazine derivatives that can be produced, starting with hydrazine by substituting one or several hydrogen atoms. This includes both acyclic and cyclic compounds, e.g. saturated tripartite compounds. Consequently, in a compound of formula (I), if E or E' is nitrogen (N), then E and E' are different from each other.

The use according to the invention of one or several binary group 15 element compounds of the general formulas (I) and/or (II) as the educt in a vapor deposition process allows a reproducible, cost-efficient representation of multinary, homogeneous and ultrapure 13/15 semiconductor connections and/or layers of a defined combination. The vapor deposition process is preferably a chemical vapor deposition, and especially a metal-organic chemical vapor deposition or a metal-organic metal-organic vapor phase epitaxy (MOVPE). The product of the vapor deposition process is preferably a 13/15 semiconductor layer.

The group 15 element compounds used according to the invention represent single source precursors (SSP) with regard to the elements of group 15. The single source precursors designated according to the invention are molecules having more than one group 15 element, especially two different group 15 elements. The group 15 elements included in the precursor may be selected and/or combined according to the desired opto-electronic characteristics of the 13/15 semiconductor to be produced and/or to be deposited on a substrate.

The group 15 element sources such as $PH_3$, $AsH_3$, $tBuPH_2$, $tBuAsH_2$ and $Me_2N$—$NH_2$ to date used for chemical vapor deposition processes each have only one group 15 element, which means that depending on the desired combination of the multinary, i.e. more than binary 13/15 semiconductor to be produced and/or deposited, several group 15 element sources have to be provided and mixed with one another. In contrast to that, the group 15 element sources of formula (I) and/or formula (II) used according to the invention advantageously include two group 15 elements each, which in most cases differ from one another. Accordingly, the advantage is the option of producing multinary 13/15 semiconductor connections and/or layers starting from the single source precursors according to the invention, without the necessity of creating a separate precursor connection for each group 15 element contained n the 13/15 semiconductor to be produced. Consequently, it is not necessary to consider various disintegration temperatures, vapor pressures and the respective varying diffusion ratios of several group 15 element sources and/or precursors in the context of planning and conducting the vapor deposition process. This makes the process particularly easy to execute in the production and/or deposition of 13/15 semiconductors.

Furthermore, the use of the binary group 15 element compounds according to the invention reduces the number of resulting by-products which consequently have to be desorbed by the 13/15 semiconductor produced and/or the respective layer, which leads to an increase in the atom efficiency and the simplification of the process.

The compounds used according to the invention have lower disintegration temperatures than the group 15 element sources such as $PH_3$, $AsH_3$, $tBuPH_2$, $tBuAsH_2$ previously used in chemical vapor deposition processes. In the case of the group 15 element compounds with E=E' to be used according to the invention, the lower disintegration temperatures can be attributed to the respective lower E-E' bonding. Furthermore, it is possible to do without the very toxic group 15 element precursors such as, for example, phosphine ($PH_3$) and arsine ($AsH_3$). This makes the vapor deposition process comparably energy-saving and thus cost-efficient at low process temperatures as well a process that may be executed in a safe, healthy and environmentally friendly way.

The selection may be effected from a plurality of single source precursors according to the invention, wherein the relationship of the group 15 elements that should be included in the 13/15 semiconductor to be produced can already be preset by the by the composition of the single source precursor. This allows the production of 13/15 semiconductor compounds and/or layers with defined, presettable opto-electronic characteristics. For example, the representation of ternary 13/15 semiconductor compounds and/or layers using the group 15 element compounds according to the invention, e.g. $Ga(E_xE'_{1-x})$ (E≠E'; 0<x<1), is possible in a simple, atom-efficient and cost-efficient manner. The same is true for the production of quaternary 13/15 semiconductor compounds and/or layers, e.g. $Ga_nIn_{1-n}E_xE'_{1-x}$ (E≠E'; 0<x<1) and $Ga(As_{1-(x+y)}N_xP_y)$ (0<x<1 and 0<y<1).

A particularly preferred embodiment of the binary group 15 element compounds of the general formula (I) and/or (II) according to the invention provides the selection of nitrogenous single source precursors such as $tBu_2As$—$NH_2$ or $HN(SbtBu_2)_2$ that have no nitrogen-bound carbon. These binary group 15 element sources have all the advantageous characteristics of single source precursors, such as, for example, high vapor pressure, low toxicity, simple producibility, easy handling and the existence of a good leaving group without, however, containing a nitrogen-bound carbon atom. It is possible to renounce the addition of an organically substituted nitrogen compound such as 1.1 dimethyl hydrazine as the nitrogen source. Consequently, such compounds are particularly suitable for the representation of ultrapure nitrogenous 13/15 semiconductors and/or layers. It is particularly advantageous that 13/15 semiconductors and/ or 13/15 semiconductor layers are obtained with the use of the compounds according to the invention that—compared to the 13/15 semiconductors and/or 13/15 semiconductor levels produced according to the previous production methods—have a drastically reduced level of carbon content since the use of carbonic nitrogen sources is waived. Carbon contaminations possibly contained in the 13/15 semiconductors and/or 13/15 semiconductor layers that are produced usually originate from the group 13 element source or sources that are usually organically substituted.

The single source precursors provided according to the invention may also be used with one or several other group 15 element sources according to the invention or already known. This may be particularly advantageous in the case of nitrogenous binary group 15 element compounds of the formula (I) or (II). The controllable addition of one or several other group 15 element sources may influence and fine tune the nitrogen content of the 13/15 semiconductor to be produced and/or deposited deriving from the nitrogenous binary group 15 element compound. It is in particular possible to produce and/or deposit 13/15 semiconductors that have a different relation between the group 15 elements than the one that would be obtained in the case of the exclusive use of binary group 15 element compounds. For example, the nitrogen content in the production of $Ga(As_{1-x}N_x)$ ($0<x<1$) usually assumes a lower level than the arsenic content. Adding another group 15 element source such as, for example, the arsenic source $tBuAsH_2$ allows for a further reduction of the nitrogen content of $Ga(As_{1-x}N_x)$ ($0<X<1$) compared to the arsenic content. This may be attributed to the fact that the nitrogen atoms have to compete with the arsenic atoms from the additional arsenic source. Accordingly it is possible to vary and/or fine tune the optoelectronic characteristics of the 13/15 semiconductors to be produced and/or deposited to an even larger extent.

On the whole, it is possible to realize a reproducible and/or deposition of multinary, homogeneous and ultrapure 13/15 semiconductors of a defined combination at relatively low process temperatures, starting from the binary group 15 element compounds according to the invention. The group 15 element precursors according to the invention allow the simple, secure, comparably atom-efficient and relatively energy-efficient production of a 13/15 semiconductor and/or a respective layer.

In one advantageous embodiment of the use according to the invention, the educt is a binary group 15 element compound of the general formula (I) and $R^1$ and $R^2$ are selected independently from one another from the group consisting of an alkyl radical (C1-C10) and an aryl group, and $R^3=R^4=H$.

Specifically, $R^1$ and $R^2$ are the same or different and are selected from the group consisting of C1 to C6 alkyl radical and C1 to C8 aryl radical. In particular, $R^1$ and $R^2$ are the same or different and are selected from the group consisting of C1 to C4 alkyl radical and C1 to C6 aryl radical. More specifically, $R^1$ and $R^2$ are the same or different and are selected from the group consisting of methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl ($C_6H_5$) or ortho- meta- and para-toluyl.

The alkyl or aryl groups can be substituted. In particular, they may be fluorinated or perfluorinated. In this case, $R^1$ and $R^2$ are, in particular, trifluormethyl ($CF_3$) or pentafluorphenyl ($C_6F_5$). In particular, $R^1$ and $R^2$ are the same. In specific embodiments, $R^1$ and $R^2$ are tBu, iPr, trifluoromethyl or phenyl.

In another specific embodiment, E and E' are different from each other. In another specific embodiment, E is selected from the group consisting of P, As and Sb. In yet another specific embodiment, E' is selected from the group consisting of N, P and As, more specifically, E' is N. In a further specific embodiment, E is selected from the group consisting of P, As, Sb and Bi, in particular P, As and Sb, and E' is N. In this embodiment, tBu can be advantageously employed as both $R^1$ and $R^2$.

The alkyl and/or aryl groups may be substituted, e.g. partly fluorinated or perfluorinated. The binary group 15 element compound of the general formula (I) is preferably selected from the group consisting of $tBu_2P—NH_2$, $(CF_3)_2P—NH_2$, $(C_6H_5)_2P—NH_2$, $tBu_2P—AsH_2$, $tBu_2As—NH_2$, $tBu_2As—PH_2$, $(C_6H_5)_2As—PH_2$, $tBu_2Sb—NH_2$ and $tBu_2Sb—PH_2$. All these single source precursors are suitable for the production and/or deposition of a plurality of multinary 13/15 semiconductors.

The nitrogenous group 15 element compounds $tBu_2P—NH_2$, $(CF_3)_2P—NH_2$, $(C_6H_5)_2P—NH2$, $tBu_2As—NH_2$ and $tBu_2Sb—NH_2$ are particularly suitable for the reproducible representation and/or deposition of ultrapure nitrogenous 13/15 semiconductor layers with drastically reduced carbon content—compared to a 13/15 semiconductor and/or 13/15 semiconductor layer produced according to known production methods—as they do not have any nitrogen-bound carbon atom. Should carbon contaminations possibly be contained in the 13/15 semiconductors and/or 13/15 semiconductor layers that are produced, they usually derive from the group 13 element source or sources that are usually organically substituted.

The binary group 15 element compound $tBu_2As—NH_2$ (DTBAA=Di-tertbutylaminoarsan) may, for example, be used as a source or nitrogen and arsenic for the synthesis of $Ga(As_{1-x}N_x)$ layers ($0<X<1$), with a potential gallium source being e.g. trimethylgallium ($Me_3Ga$), tri-tertbutylgallium ($tBu_3Ga$) or tri-ethylgallium ($Et_3Ga$), and the deposition may occur on GaAs as the substrate. This makes it possible to waive the use of an organically substituted nitrogen compound such as 1.1 dimethyl hydrazine as the nitrogen source, which drastically reduces nitrogen contaminations—compared to the 13/15 semiconductors and/or 13/15 semiconductor layers produced with the known production methods. Any carbon contaminations possibly contained in the 13/15 semiconductors and/or 13/15 semiconductor layers that are produced usually derive from the group 13 element source or sources that are normally organically substituted.

In as much as the only source of arsenic is the binary group 15 element compound $tBu_2As—NH_2$, the relationship of the group 15 elements that should be contained in the 13/15 semiconductor and/or the 13/15 semiconductor layer to be produced—in this case nitrogen and arsenic—is mainly preset by the composition of the single source precursor $tBu_2As—NH_2$. The group 15 element/group 15 element relation, e.g. the relation As/N in the 13/15 semiconductor and/or the 13/15 semiconductor layer may, however, be influenced by a variation of the process parameters, e.g. the partial pressure of the binary group 15 element sources in the reactor or the process temperature. In addition to the group 15 element compound $tBu_2As—NH_2$, one or several other group 15 element compounds according to the invention or already known may be used, e.g. the known non-binary group 15 element compound $tBuAsH_2$ as an additional source of arsenic or the known non-binary group 15 element compound tBuPH$_2$ as a source of phosphorus. The use of tBu$_2$As—NH$_2$ as binary group 15 element compounds with the addition of one or several group 15 element compounds allows the production of Ga(As$_{1-x}$N$_x$) layers (0<x<1) which have a lower nitrogen content compared to the exclusive use of tBu$_2$As—NH$_2$ as the source of nitrogen and arsenic. This can be attributed to the fact that the nitrogen atoms have to compete with the group 15 element atoms from the additional group 15 element source, e.g. from a source of arsenic or phosphorus. On the whole, the combination and thus the opto-electronic characteristics of the 13/15 semiconductor and/or the 13/15 semiconductor layer may be varied and/or fine-tuned to a large degree.

In another embodiment of the use according to the invention, the educt is a binary group 15 element compound of the general formula (I) and
  R$^1$, R$^2$ and R$^4$ are selected independently from one another from the group consisting of an alkyl radical (C1-C10) and an aryl group, and
  R$^3$=H.

Specifically, R$^1$, R$^2$ and R$^4$ are the same or different and are selected from the group consisting of C1 to C6 alkyl radical and C1 to C8 aryl radical. In particular, R$^1$, R$^2$ and R$^4$ are the same or different and are selected from the group consisting of C1 to C4 alkyl radical and C1 to C6 aryl radical. More specifically, R$^1$, R$^2$ and R$^4$ are the same or different and are selected from the group consisting of methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl (C$_6$H$_5$) or ortho- meta- and para-toluyl.

The alkyl or aryl groups can be substituted, particularly fluorinated or perfluorinated. In this case, R$^1$, R$^2$ and R$^4$ are, in particular, trifluormethyl (CF$_3$) or pentafluorphenyl (C$_6$F$_5$). In one embodiment, R$^1$, R$^2$ and R$^4$ are the same. In specific embodiments, R$^1$, R$^2$ and R$^4$ are, independently of each other, Me, tBu, iPr, trifluormethyl or phenyl.

In a specific embodiment, E and E' are different. In another specific embodiment, E is selected from the group consisting of As and Sb. In yet another specific embodiment, E' is selected from the group consisting of N, P, Sb and Bi.

Even more specifically, if E' is Sb or Bi, then R$^4$ is tBu.

The alkyl and/or aryl groups may be substituted, e.g. partly fluorinated or perfluorinated. The binary group 15 element compound of the general formula (I) is preferably selected from the group consisting of tBu$_2$As—PHMe, tBu$_2$Sb—NHtBu, tBu$_2$Sb—PHtBu and tBu$_2$Sb—NHiPr. These single source precursors may be used for the reproducible representation and/or deposition of various homogeneous, definable 13/15 semiconductors.

Another embodiment of the use according to the invention provides that the educt is a binary group 15 element compound with the general formula (I), and R$^1$, R$^2$, R$^3$ and R$^4$ have been independently selected from the group consisting of an alkyl radical (C1-C10) and an aryl group. The alkyl and/or aryl groups may be substituted, e.g. partly fluorinated or perfluorinated. The binary group 15 element compound of the general formula (I) is preferably selected from the group consisting of Me$_2$As—AsMe$_2$, tBu$_2$Sb—NMe$_2$, iPr$_2$Sb—PMe$_2$, Et$_2$Sb—NMe$_2$, Et$_2$Sb—P(C$_6$H$_5$)$_2$, tBu$_2$Bi—PtBu$_2$ and tBu$_2$Bi—AstBu$_2$.

These compounds are all suitable for the reproducible generation and/or deposition of a plurality of homogeneous multinary 13/15 semiconductors of defined combination.

In another embodiment of the use according to the invention, the educt is a binary group 15 element compound of the general formula (II) and R$^5$=H. In this case, the binary group 15 element compound of the general formula (II) is preferably selected from the group consisting of HP(AstBu$_2$)$_2$ and HN(SbtBu$_2$)$_2$. Both single source precursors are suitable for the reproducible representation and/or deposition of homogeneous, defined and ultrapure 13/15 semiconductors. The binary group 15 element compound HN(SbtBu$_2$)$_2$ is particularly suitable for the reproducible manufacture of nitrogenous 13/15 semiconductors and/or 13/15 semiconductor layers of the defined composition. It is particularly advantageous that 13/15 semiconductors and/or 13/15 semiconductor layers are obtained with the use of the binary group 15 element compounds according to the invention that—compared to the 13/15 semiconductors and/or 13/15 semiconductor levels produced according to the previous production methods—have a drastically reduced level of carbon content since the use of carbonic nitrogen sources is waived. Should carbon contaminations possibly be contained in the 13/15 semiconductors and/or 13/15 semiconductor layers that are produced, they usually derive from the group 13 element source or sources that are usually organically substituted.

In another embodiment of the use according to the invention, the educt is a binary group 15 element compound of the general formula (II) and
  R$^5$ is selected from the group consisting of an alkyl radical (C1-C10) and an aryl group, and
  R$^6$=R$^7$=H.

Specifically, R$^5$ is selected from the group consisting of C1 to C6 alkyl radical and C1 to C8 aryl radical. In particular, R$^5$ is selected from the group consisting of C1 to C4 alkyl radical and C1 to C6 aryl radical. More specifically, R$^5$ is selected from the group consisting of methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl (C$_6$H$_5$) or ortho- meta- and para-toluyl.

The alkyl and/or aryl groups may be substituted, e.g. partly fluorinated or perfluorinated. In this case, R$^5$ may be selected from the group consisting of trifluormethyl (CF$_3$) or pentafluorphenyl (C$_6$F$_5$). In specific embodiments, R$^5$ may be selected from Me, tBu, trifluormethyl or phenyl.

In another specific embodiment, E is selected from the group consisting of P and As. In yet another specific embodiment, E' is N.

The binary group 15 element compound of the general formula (II) is preferably selected from the group consisting of tBuP(NH$_2$)$_2$, tBuAs(NH$_2$)$_2$ and (C$_6$H$_5$)P(NH$_2$)$_2$. These group 15 element sources are suitable for the reproducible representation and/or deposition of nitrogenous, homogeneous, ultrapure 13/15 semiconductors of the defined combination. It is particularly advantageous that 13/15 semiconductors and/or 13/15 semiconductor layers obtained with the use of the binary group 15 element compounds according to the invention that—compared to the 13/15 semiconductors and/or 13/15 semiconductor levels produced according to the previous production methods—have a drastically reduced level of carbon content since the use of carbonic nitrogen sources is waived. Carbon contaminations possibly contained in the 13/15 semiconductors and/or 13/15 semiconductor layers that are produced usually originate from the group 13 element source or sources that are usually organically substituted.

In another embodiment of the use according to the invention, the educt is a binary group 15 element compound of the general formula (II) and R⁵ and R⁷ are selected independently from one another from the group consisting of an alkyl radical (C1-C10) and an aryl group, and

R⁶=H.

Specifically, R⁵ and R⁷ are the same or different and are selected from the group consisting of C1 to C6 alkyl radical and C1 to C8 aryl radical. In particular, R⁵ and R⁷ are the same or different and are selected from the groups consisting of C1 to C4 alkyl radical and C1 to C6 aryl radical. More specifically, R⁵ and R⁷ are the same or different and are selected from the group consisting of methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl ($C_6H_5$) or ortho- meta- and para-toluyl.

The alkyl or aryl groups can be substituted, particularly fluorinated or perfluorinated and in this case, R⁵ and R⁷ are, in particular, trifluormethyl ($CF_3$) or pentafluorphenyl ($C_6F_5$). In a specific embodiment, R⁵ and R⁷ are different. In another specific embodiment, R⁵ and R⁷ may be selected from Me, Et, nBu, tBu, trifluormethyl or phenyl.

In another specific embodiment, E is selected from the group consisting of P, As and Sb and more specifically, may be P. In yet another specific embodiment, E' is selected from the group consisting of N, P and As and more specifically is As.

The alkyl and/or aryl groups may be substituted, e.g. partly fluorinated or perfluorinated. The binary group 15 element compound of the general formula (II) is preferably selected from the group consisting of $nBuP(AsHMe)_2$ and $(C_6H_5)P(AsHMe)_2$. Both single source precursors are suitable for the reproducible production of homogeneous, defined and ultrapure 13/15 semiconductors and/or layers.

In another embodiment of the use according to the invention, the educt is a binary group 15 element compound of the general formula (II) and R⁵=H, and R⁶ and R⁷ are selected from the group consisting of an alkyl radical (C1-C10) and an aryl group, Specifically, R⁶ and R⁷ are selected from the group consisting of C1 to C6 alkyl radical and C1 to C8 aryl radical. In particular, R⁶ and R⁷ are selected from the group consisting of C1 to C4 alkyl radical and C1 to C6 aryl radical. More specifically, R⁶ and R⁷ are selected from the group consisting of methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl ($C_6H_5$) or ortho- meta- and para-toluyl. The alkyl and/or aryl groups may be substituted, e.g. partly fluorinated or perfluorinated. In this case, R⁶ and R⁷ may be selected from the group consisting of trifluormethyl ($CF_3$) or pentafluorphenyl ($C_6F_5$). In a specific embodiment, R⁶ and R⁷ are the same. In specific embodiments, R⁶ and R⁷ are may be selected from Me, tBu or phenyl.

In another specific embodiment, E is selected from the group consisting of P and As. In yet another specific embodiment, E' is N.

The binary group 15 element compound of the general formula (II) is preferably selected from the group consisting of $HP(AstBu_2)_2$, $HN(SbtBu_2)_2$, $HP(N(tBu)_2)_2$, $HAs(N(tBu)_2)_2$ and $HP(N(C_6H_5)_2)_2$. These group 15 element sources are suitable for the reproducible representation and/or deposition of nitrogenous, homogeneous, ultrapure 13/15 semiconductors of the defined combination. It is particularly advantageous that 13/15 semiconductors and/or 13/15 semiconductor layers obtained with the use of the binary group 15 element compounds according to the invention that—compared to the 13/15 semiconductors and/or 13/15 semiconductor levels produced according to the previous production methods—have a drastically reduced level of carbon content since the use of carbonic nitrogen sources is waived. Carbon contaminations possibly contained in the 13/15 semiconductors and/or 13/15 semiconductor layers that are produced usually originate from the group 13 element source or sources that are usually organically substituted.

Another embodiment of the use according to the invention provides that the educt is a binary group 15 element compound with the general formula (II), and R⁵, R⁶ and R⁷ are independently selected from the group consisting of an alkyl radical (C1-C10) and an aryl group.

The alkyl and/or aryl groups may be substituted, e.g. partly fluorinated or perfluorinated. The binary group 15 element compound of the general formula (II) is preferably selected from the group consisting of $tBuAs(NMe_2)_2$, $m$-$F_3CC_6H_4As(NMe_2)_2$ and $tBuAs(PMe_2)_2$. All of these compounds are suitable for the reproducible generation and/or deposition of a plurality of homogeneous multinary 13/15 semiconductors of defined combination.

The use of the group 15 element compounds as educt in a vapor deposition process as described above does also encompass a method for vapor deposition, wherein a compound of formula (I) or formula (II) is employed as an educt.

In this way, a 13/15 semiconductor layer can be produced by this method for vapor deposition, using at least one binary group 15 element compound as the educt in a vapor deposition process according to one of the embodiments specified above.

Specifically, the method for vapor deposition, wherein a compound of formula (I) or formula (II) is employed as an educt, which is encompassed by the use of the group 15 element compounds of formula (I) or formula (II) as educt in a vapor deposition process as described above may comprise the steps of Providing at least one group 15 element compound of formula (I) or formula (II) described above;

Exposing the group 15 element compound of formula (I) or formula (II) to conditions suitable for deposition of a 13/15 semiconductor layer; and Deposition of a 13/15 semiconductor layer.

More specifically, the method for vapor deposition, wherein a compound of formula (I) or formula (II) is employed as an educt, which is encompassed by the use of the group 15 element compounds of formula (I) or formula (II) as educt in a vapor deposition process as described above may comprise the steps of Providing at least one group 15 element compound of formula (I) or formula (II) described above;

Providing at least one group 13 element compound;

Exposing both the group 15 element compound or compounds of formula (I) or formula (II) and the group 13 compound or compounds to conditions suitable for deposition of a 13/15 semiconductor layer; and Deposition of a 13/15 semiconductor layer.

In the method, the group 15 element compounds of formula (I) or formula (II) can be all compounds described generically or specifically in various embodiments above and are, generally speaking, compounds according to the general formula $$R^1R^2E\text{-}E'R^3R^4 \qquad (I),$$

wherein

R¹, R², R³ and R⁴ are selected independently from one another from the group consisting of H, an alkyl radical (C1-C10) and an aryl group, and E and E' are selected independently from one another from the group consisting of P, As, Sb and Bi, wherein E≠E', or according to the general formula $$R^5E(E'R^6R^7)_2 \quad (II),$$

wherein

R⁵, R⁶, and R⁷ are selected independently from one another from the group consisting of H, an alkyl radical (C1-C10) and an aryl group, E is selected from the group consisting of N, P, As, Sb and Bi, and E' is selected from the group consisting of P, As, Sb and Bi, wherein E≠E'.

Hydrazine (H₂N—NH₂) and its derivatives are not the subject matter of the invention.

Specifically, R¹, R², R³, R⁴, R⁵, R⁶ and R⁷ are the same or different and are selected from the group consisting of hydrogen (H), C1 to C6 alkyl radical and C1 to C8 aryl radical. In particular, R¹, R², R³, R⁴, R⁵, R⁶ and R⁷ are the same or different and are selected from the group consisting of hydrogen (H), C1 to C4 alkyl radical and C1 to C6 aryl radical. More specifically, R¹, R², R³, R⁴, R⁵, R⁶ and R⁷ are the same or different and are selected from the group consisting of hydrogen (H), methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl (C₆H₅) or ortho- meta- and para-toluyl.

The alkyl and/or aryl groups may be substituted, e.g. partly fluorinated or perfluorinated. In this case, R¹, R², R³, R⁴, R⁵, R⁶ and R⁷ may be, in particular, trifluormethyl (CF₃) or pentafluorphenyl (C₆F₅). In a specific embodiment, E and E' are different and one of E or E' is N. In another specific embodiment of a compound of formula (I), R¹ and R² are hydrogen (H), if R³ and R⁴ are different from hydrogen, or R³ and R⁴ are hydrogen, if R¹ and R² are different from hydrogen.

The invention does not concern the use of hydrazine (H₂N—NH₂) and its derivatives, especially 1.1 dimethyl hydrazine and tertiary butyl hydrazine as the educt in a vapor deposition process. These compounds are regarded as hydrazine derivatives that can be produced, starting with hydrazine by substituting one or several hydrogen atoms. This includes both acyclic and cyclic compounds, e.g. saturated tripartite compounds. Consequently, in a compound of formula (I), if E or E' is nitrogen (N), then E and E' are different from each other.

The group 15 element compounds used according to the invention represent single source precursors (SSP) with regard to the elements of group 15. This means that the single source precursors provided according to the invention each have more than one group 15 element, wherein these are two different group 15 elements. The group 15 elements included in the precursor may be selected or combined according to the characteristics, especially the opto-electronic characteristics that the 13/15 semiconductor that is to be produced and/or deposited on a substrate should have.

In the method for vapor deposition, wherein a compound of formula (I) or formula (II) is employed as an educt, the group 15 element compound of formula (I) or formula (II) may be employed as single compound, as a mixture with each other or with other group 15 compounds which are not subject of this patent application, such as PH₃, AsH₃, tBuPH₂, tBuAsH₂ and Me₂NNH₂.

Suitable group 13 compounds are, for example, trimethyl indium (Me₃In) trimethyl gallium (Me₃Ga), tri-tertbutyl gallium (tBu₃Ga) or triethyl gallium (Et₃Ga).

Exposing both the group 15 element compound or compounds of formula (I) or formula (II) and the group 13 compound or compounds to conditions suitable for deposition of a 13/15 semiconductor layer is generally known in the art as repeatable vapor deposition processes, like a chemical vapor deposition process, such as methods known as metal-organic chemical vapor deposition (MOCVD) or metal-organic vapor phase epitaxy (MOVPE), which usually yield in deposition of layers that are characterized by being homogeneous, defined and ultrapure.

A binary group 15 element compound tBu₂As—NH₂ (DTBAA=Di-tertbutylaminoarsan) may, for example, be used as a source or nitrogen and arsenic for the synthesis of Ga(As₁₋ₓNₓ) layers (0<X<1), with a potential gallium source being e.g. trimethylgallium (Me₃Ga), tri-tertbutyl-gallium (tBu₃Ga) or tri-ethylgallium (Et₃Ga), and the deposition may occur on GaAs as the substrate. This makes it possible to waive the use of an organically substituted nitrogen compound such as 1.1 dimethyl hydrazine as the nitrogen source, which drastically reduces carbon contaminations—compared to the 13/15 semiconductors and/or 13/15 semiconductor layers produced with the known production methods. Any carbon contaminations possibly contained in the 13/15 semiconductors and/or 13/15 semiconductor layers that are produced usually derive from the group 13 element source or sources that are normally organically substituted.

In as much as the only source of arsenic is the binary group 15 element compound tBu₂As—NH₂, the relationship of the group 15 elements that should be contained in the 13/15 semiconductor and/or the 13/15 semiconductor layer to be produced—in this case nitrogen and arsenic—is mainly preset by the composition of the single source precursor tBu₂As—NH₂. The group 15 element/group 15 element relation, e.g. the relation As/N in the 13/15 semiconductor and/or the 13/15 semiconductor layer may, however, be influenced by a variation of the process parameters, e.g. the partial pressure of the binary group 15 element sources in the reactor or the process temperature. In addition to the group 15 element compound tBu₂As—NH₂, one or several other group 15 element compounds according to the invention or already known may be used, e.g. the known non-binary group 15 element compound tBuAsH₂ as an additional source of arsenic or the known non-binary group 15 element compound tBuPH₂ as a source of phosphorus. The use of tBu₂As—NH₂ as binary group 15 element compounds with the addition of one or several group 15 element compounds allows the production of Ga(As₁₋ₓNₓ) layers (0<x<1) which have a lower nitrogen content compared to the exclusive use of tBu₂As—NH₂ as the source of nitrogen and arsenic. This can be attributed to the fact that the nitrogen atoms have to compete with the group 15 element atoms from the additional group 15 element source, e.g. from a source of arsenic or phosphorus. On the whole, the combination and thus the opto-electronic characteristics of the 13/15 semiconductor and/or the 13/15 semiconductor layer may be varied and/or fine-tuned to a large degree.

This purpose is furthermore met by a 13/15 semiconductor layer that is producible in a vapor deposition process using at least one binary group 15 element compound as the educt in a vapor deposition process according to one of the embodiment examples described above.

This refers to a 13/15 semiconductor layer that is producible in a vapor deposition process using at least one binary group 15 element compound as the educt,
wherein at least one binary group 15 element compound has the general formula $$R^1R^2E-E'R^3R^4 \qquad (I),$$

wherein
R$^1$, R$^2$, R$^3$ and R$^4$ are selected independently from one another from the group consisting of H, an alkyl radical (C1-C10) and an aryl group, and
E and E' are selected independently from one another from the group consisting of N, P, As, Sb and Bi, wherein E=E' or E≠E',
and/or
wherein at least one binary group 15 element compound has the general formula $$R^5E(E'R^6R^7)_2 \qquad (II),$$

wherein
R$^5$, R$^6$ and R$^7$ are selected independently from one another from the group consisting of H, an alkyl radical (C1-C10) and an aryl group, and
E and E' are selected independently from one another from the group consisting of N, P, As, Sb and Bi, wherein E=E' or E≠E',
Specifically, R$^1$, R$^2$, R$^3$, R$^4$, R$^5$, R$^6$ and R$^7$ are the same or different and are selected from the group consisting of hydrogen (H), C1 to C6 alkyl radical and C1 to C8 aryl radical. In particular, R$^1$, R$^2$, R$^3$, R$^4$, R$^5$, R$^6$ and R$^7$ are the same or different and are selected from the group consisting of hydrogen (H), C1 to C4 alkyl radical and C1 to C6 aryl radical. More specifically, R$^1$, R$^2$, R$^3$, R$^4$, R$^5$, R$^6$ and R$^7$ are the same or different and are selected from the group consisting of hydrogen (H), methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl (C$_6$H$_5$) or ortho- meta- and para-toluyl.

The alkyl and/or aryl groups may be substituted, e.g. partly fluorinated or perfluorinated. In this case, R$^1$, R$^2$, R$^3$, R$^4$, R$^5$, R$^6$ and R$^7$ may be, in particular, trifluormethyl (CF$_3$) or pentafluorphenyl (C$_6$F$_5$).

The invention does not concern the use of hydrazine (H$_2$N—NH$_2$) and its derivatives, especially 1.1 dimethyl hydrazine and tertiary butyl hydrazine as the educt in a vapor deposition process. These compounds are regarded as hydrazine derivatives that can be produced, starting with hydrazine by substituting one or several hydrogen atoms. This includes both acyclic and cyclic compounds, e.g. saturated tripartite compounds.

The 13/15 semiconductor layer according to the invention, produced in a repeatable vapor deposition process, preferably in a chemical vapor deposition, especially in a metal-organic chemical vapor deposition (MOCVD) or a metal-organic vapor phase epitaxy (MOVPE) is characterized by being homogeneous, defined and ultrapure.

In preparation for the production of the 13/15 semiconductor layer according to the invention, one may choose from a plurality of binary group 15 element compounds of the general formulas (I) and (II) according to the invention. The composition of the single source precursor mainly determines, especially by means of the respective selection of the binary group 15 elements, the relationship of the group 15 elements to be contained in the 13/15 semiconductor layer.

The single source precursors provided according to the invention may also be used with one or several other group 15 element sources according to the invention or already known. This may be particularly advantageous in the case of nitrogenous binary group 15 element compounds of the formula (I) or (II). A controllable addition of one or several other group 15 element sources according to the invention or already known may influence and fine tune the nitrogen content of the 13/15 semiconductor to be produced and/or deposited deriving from the nitrogenous binary group 15 element compound. It is in particular possible to produce or deposit 13/15 semiconductors that do not feature the group 15 elements contained in the binary nitrogenous group 15 element compound at the same ratio that is mainly preset by the composition of the single source precursor. Inasmuch as the only source of arsenic is, for example, the binary group 15 element compound tBu$_2$As—NH$_2$, the relationship of the group 15 elements that should be contained in the 13/15 semiconductor and/or the 13/15 semiconductor layer to be produced and/or deposited—in this case nitrogen and arsenic—is mainly prescribed by the composition of the single source precursor tBu$_2$As—N$_2$. The group 15 element/group 15 element relation, e.g. the relation As/N in the 13/15 semiconductor to be produced and/or the 13/15 semiconductor layer to be deposited may, however, be influenced by a variation of the process parameters, e.g. the partial pressure of the binary group 15 element sources in the reactor or the process temperature. In addition to the group 15 element compound tBu$_2$As—NH$_2$, one or several other group 15 element compounds according to the invention or already known may be used, e.g. the known non-binary group 15 element compound tBuAsH$_2$ as an additional source of arsenic or the known non-binary group 15 element compound tBuPH$_2$ as a source of phosphorus. If tBu$_2$As—NH$_2$ is used as the binary group 15 element compound with the addition of one or several group 15 element compounds, it is possible to create Ga(As$_{1-x}$N$_x$) layers (0<x<1), which—compared with the exclusive use of tBu$_2$As—NH$_2$ as the source of nitrogen and arsenic—have a lower nitrogen content. This can be attributed to the fact that the nitrogen atoms have to compete with the group 15 element atoms from the additional group 15 element source, e.g. from a source of arsenic or phosphorus. Accordingly it is possible to vary and/or fine tune the opto-electronic characteristics of the 13/15 semiconductors to be produced and/or deposited to an even larger extent.

This allows the production of 13/15 semiconductor compounds and/or layers with defined, settable opto-electronic characteristics 5. Furthermore, the use of binary group 15 element sources as provided according to the invention allows the representation of multinary 13/15 semiconductor layers at relatively low process temperatures, which contributes to an improvement of the energy efficiency and thus in general to process optimization. In addition, the process is particularly easy and safe in execution, as well as atom- and energy-efficient and therefore, on the whole, cost-efficient.

The purpose is further met by the binary group 15 element compounds according to the general formula $$R^1R^2E-E'R^3R^4 \qquad (I),$$

wherein
R$^1$, R$^2$, R$^3$ and R$^4$ are selected independently from one another from the group consisting of H, an alkyl radical (C1-C10) and an aryl group, and E and E' are selected independently from one another from the group consisting of P, As, Sb and Bi, wherein E≠E', or according to the general formula $R^5E(E'R^6R^7)_2$ (II), wherein $R^5$, $R^6$, and $R^7$ are selected independently from one another from the group consisting of H, an alkyl radical (C1-C10) and an aryl group, E is selected from the group consisting of N, P, As, Sb and Bi, and E' is selected from the group consisting of P, As, Sb and Bi, wherein E≠E'.

Hydrazine ($H_2N$—$NH_2$) and its derivatives are not the subject matter of the invention. Specifically, $R^1$, $R^2$, $R^3$, $R^4$, $R^5$, $R^6$ and $R^7$ are the same or different and are selected from the group consisting of hydrogen (H), C1 to C6 alkyl radical and C1 to C8 aryl radical. In particular, $R^1$, $R^2$, $R^3$, $R^4$, $R^5$, $R^6$ and $R^7$ are the same or different and are selected from the group consisting of hydrogen (H), C1 to C4 alkyl radical and C1 to C6 aryl radical. More specifically, $R^1$, $R^2$, $R^3$, $R^4$, $R^5$, $R^6$ and $R^7$ are the same or different and are selected from the group consisting of hydrogen (H), methyl (Me), ethyl (Et), n-propyl (nPr), isopropyl (iPr), cyclopropyl, butyl (nBu), isobutyl (iBu or 2-methylpropyl), sec-butyl (secBu), tert.-butyl (tBu or 2-methylpropyl), cyclopropyl, phenyl ($C_6H_5$) or ortho- meta- and para-toluyl.

The alkyl and/or aryl groups may be substituted, e.g. partly fluorinated or perfluorinated. In this case, $R^1$, $R^2$, $R^3$, $R^4$, $R^5$, $R^6$ and $R^7$ may be, in particular, trifluormethyl ($CF_3$) or pentafluorphenyl ($C_6F_5$).

The group 15 element compounds used according to the invention represent single source precursors (SSP) with regard to the elements of group 15. This means that the single source precursors provided according to the invention each have more than one group 15 element, wherein these are two different group 15 elements. The group 15 elements included in the precursor may be selected or combined according to the characteristics, especially the opto-electronic characteristics that the 13/15 semiconductor that is to be produced and/or deposited on a substrate should have.

The group 15 element sources such as $PH_3$, $AsH_3$, $tBuPH_2$, $tBuAsH_2$ and $Me_2NNH_2$ used until now for chemical vapor deposition processes, each have only one group 15 element, which means that depending on the desired combination of the 13/15 semiconductor to be produced and/or deposited, several group 15 element sources have to be provided and mixed with one another. In contrast, the group 15 element sources of formula (I) and/or (II) used according to the invention advantageously include two group 15 elements that differ from one another. Accordingly, the advantage is the option of producing multinary 13/15 semiconductor connections and/or layers starting from the single source precursors according to the invention, without the necessity of creating a separate precursor connection for each group 15 element contained in the 13/15 semiconductor to be produced. Consequently, it is not necessary to consider various disintegration temperatures, vapor pressures and the respective varying diffusion ratios of several group 15 element sources and/or precursors in the context of planning and conducting the vapor deposition process. This makes the process particularly easy to execute in the production and/or deposition of 13/15 semiconductors.

Furthermore, the use of the binary group 15 element compounds according to the invention reduces the number of resulting by-products which consequently have to be desorbed by the 13/15 semiconductor produced and/or the respective layer, which leads to an increase in the atom efficiency and the simplification of the process.

The compounds according to the invention have lower disintegration temperatures than the group 15 element sources such as $PH_3$, $AsH_3$, $tBuPH_2$, $tBuAsH_2$ previously used in chemical vapor deposition processes. Furthermore, the group 15 element precursors according to the invention are not toxic compared to phosphine ($PH_3$) and arsine ($AsH_3$). With the use of the group 15 element precursors according to the invention, the vapor deposition process may be conducted at relatively low process temperatures in a comparably energy- and thus cost-efficient way, as well as in a safe, healthy and environmentally-friendly manner.

The selection may be effected from a plurality of single source precursors according to the invention, wherein the relationship of the group 15 elements that should be included in the 13/15 semiconductor to be produced is already preset substantially indicated by the combination of the single source precursor. This allows the production of 13/15 semiconductor compounds and/or layers with defined, presettable opto-electronic characteristics. For example, the representation of ternary 13/15 semiconductor compounds and/or layers using the group 15 element compounds according to the invention, e.g. $Ga(E_xE'_{1-x})$ (E≠E'; 0<x<1), is possible in a simple, atom-efficient and cost-efficient manner. The same is true for the production of quaternary 13/15 semiconductor compounds and/or layers, e.g. $Ga_n In_{1-n}E_xE'_{1-x}$ (E≠E'; 0<x<1) and $Ga(As_{1-(x+y)}N_xP_y)$ (0<x<1 and 0<y<1).

In a particularly preferred embodiment of the binary group 15 element compounds of the general formula (I) and/or (II) according to the invention, these compounds are nitrogenous single source precursors such as $tBu_2As$—$NH_2$ or $HN(SbtBu_2)_2$ that have no nitrogen-bound carbon. These binary group 15 element sources have all the advantageous characteristics of single source precursors, such as, for example, high vapor pressure, low toxicity, simple producibility, easy handling and the existence of a good leaving group without, however, containing a nitrogen-bound carbon atom. It is possible to renounce the addition of an organically substituted nitrogen compound such as 1.1 dimethyl hydrazine as the nitrogen source. Consequently, such compounds are particularly suitable for the representation of ultrapure nitrogenous 13/15 semiconductors and/or layers. It is particularly advantageous that 13/15 semiconductors and/or 13/15 semiconductor layers are obtained with the use of the compounds according to the invention that—compared to the 13/15 semiconductors and/or 13/15 semiconductor levels produced according to the previous production methods—have a drastically reduced level of carbon content since the use of carbonic nitrogen sources is waived. Should carbon contaminations possibly be contained in the 13/15 semiconductors and/or 13/15 semiconductor layers that are produced, they usually derive from the group 13 element source or sources that are usually organically substituted.

The single source precursors provided according to the invention may also be used with one or several other group 15 element sources according to the invention or already known. This may be particularly advantageous in the case of nitrogenous binary group 15 element compounds of the formula (I) or (II). The controllable addition of one or several other group 15 element sources may influence and fine tune the nitrogen content of the 13/15 semiconductor to be produced and/or deposited deriving from the nitrogenous binary group 15 element compound. It is in particular possible to produce or deposit 13/15 semiconductors that do not feature the group 15 elements contained in the binary nitrogenous group 15 element compound at the same ratio that is mainly preset by the composition of the single source precursor. Accordingly it is possible to vary and/or fine tune the opto-electronic characteristics of the 13/15 semiconductors to be produced and/or deposited to an even larger extent.

On the whole, it is possible to realize a reproducible production and/or deposition of multinary, homogeneous and ultrapure 13/15 semiconductors of a defined combination at relatively low process temperatures starting from the binary group 15 element compounds according to the invention. The group 15 element precursors according to the invention allow the simple, secure, comparably atom-efficient and relatively energy-efficient production of a 13/15 semiconductor and/or a respective layer.

Other characteristics, details and advantages of the invention follow from the exact wording of the claims as well as from the following description of the embodiment examples based on the illustrations. They show:

SYNTHESIS OF GROUP 15 ELEMENT COMPOUNDS TO BE USED ACCORDING TO THE INVENTION

Example 1: Preparation of tBu$_2$As—PH$_2$ 45 ml of a solution of [LiAl(PH$_2$)$_4$] (0.091 M) in DME (4.1 mmol) are presented at −60° C. together with 30 ml THF, and subsequently 2.5 ml tBu$_2$AsCl (12.3 mmol) in 15 ml DME added drop by drop. Once this is heated to room temperature, 100 ml pentane at 0° C. are added, and the sediment generated is filtered off. The solvent is removed, and the residue dissolved in pentane and once again filtered. Once the solvent has been removed under vacuum, the product is condensed at room temperature into a template cooled to −196° C. The result is tBu$_2$As—PH2 as a clear, colorless liquid with a yield of 50%.

$^1$H-NMR (300 MHz, C$_6$D$_6$): δ=1.17 (d, $^4J_{P,H}$=0.4 Hz, 18H, CH$_3$), 2.01 (d, $^1J_{P,H}$=181.9 Hz, 2H, PH$_2$) ppm.
$^{13}$C{$^1$H}-NMR (75 MHz, C$_6$D$_6$): δ=30.5 (d, $^3J_{P,C}$=4.5 Hz, CH$_3$), 32.4 (s, C$_{quaternary}$) ppm.
$^{31}$P-NMR (121 MHz, C$_6$D$_6$): δ=−204.6 (t, $^1J_{P,H}$=181.9 Hz, PH$_2$) ppm.

Example 2: Preparation of tBu$_2$As—NH$_2$
(Documented in: O. J. Scherer, W. Janssen, J. Organomet Chem. 1969, 16, P69-P70.)

A continuous NH$_3$ stream of gas is introduced into a solution of tBu$_2$AsCl (4.0 g) in 50 ml diethyl ether for two hours at 20° C. The NH$_4$Cl sediment that occurs is subsequently removed by filtration. The solvent is then distilled from the filtrate and the residue is then subjected to precision distillation in a vacuum. The resulting compound is tBu$_2$As—NH$_2$ at a pressure of 0.002 kPa (0.02 mbar) and a temperature of 40° C. with a yield of 60%.

$^1$H-NMR (300 MHz, C$_6$D$_6$): δ=0.53 (s, br, 2H, NH$_2$), 1.06 (s, 18H, CH$_3$) ppm.
$^{13}$C{$^1$H}-NMR (75 MHz, C$_6$D$_6$): δ=28.3 (s, CH$_3$), 34.4 (s, C$_{quaternary}$) ppm.

Example 3: Preparation of tBu$_2$Sb—PH2

9.2 ml of a solution of [LiAl(PH$_2$)$_4$] in DME (1.62 mmol, 0.176 M in DME) is presented at −78° C. and 1.0 ml tBu$_2$SbCl (4.31 mmol) is added drop by drop. The milkyyellow solution is heated to room temperature after 20 minutes and stirred for another 30 minutes. The solvent is removed at a reduced pressure, and the brown residue extracted with n-pentane (20 ml) and then filtered. Once the solvent is removed at a reduced pressure, the compound tBu$_2$Sb—PH$_2$ is produced as an orange colored oil, which quickly disintegrates at room temperature, generating tBuPH$_2$, PH$_3$, (tBuSb)$_4$ and (tBu$_2$Sb)2PH, which therefore has to be stored at −80° C.

$^1$H-NMR (300 MHz, C$_6$D$_6$): δ=1.25 (s, 18H, CH$_3$), 1.63 (d, $^1J_{P,H}$=175 Hz, 2H, PH$_2$) ppm.
$^{13}$C{$^1$H}-NMR (75 MHz, C$_6$D$_6$): δ=28.0 (d, $^2J_{P,C}$=4 Hz, C(CH$_3$)$_3$), 31.9 (d, $^3J_{P,C}$=3 Hz, CH$_3$) ppm.
$^{31}$P-NMR (121 MHz, C$_6$D$_6$): δ=−244.3 (t, $^1J_{P,H}$=175 Hz, PH$_2$) ppm.

Example 4: Preparation of tBu$_2$Sb—NH$_2$ 0.26 g LiNH$_2$ (11.4 mmol) is suspended in 30 ml diethyl ether. Then, 2.81 g (10.4 mmol) tBu$_2$SbCl is dissolved and added drop by drop to 20 ml diethyl ether at −20° C. Once heated to room temperature, the solvent is removed under a high vacuum, and the residue received in 30 ml n-pentane. Once the solid is separated by centrifugation, the solvent is removed under a high vacuum. 1.91 g tBu$_2$Sb—NH$_2$ remains (yield 73%) as a colorless liquid.

$^1$H-NMR: (300 MHz, C$_6$D$_6$): δ=0.19 (s, br, NH$_2$, 2H); 1.15 (s, 18H, CH$_3$) ppm.
$^{13}$C{$^1$H}-NMR: (75 MHz, C$_6$D$_6$): δ=29.0 (s, SbC(CH$_3$)$_3$); 29.5 (s, SbC(CH$_3$)$_3$) ppm.
$^{15}$N{$^1$H}-NMR: (51 MHz, C$_6$D$_6$): δ=−11.0 (s) ppm.

Example 5: Preparation of tBu$_2$Sb—NHtBu 4.45 g tBu$_2$SbCl (16.4 mmol) is suspended in 50 ml n-pentane. The solution is cooled to 0° C. and 1.30 g tBuNHLi (16.4 mmol) added. The solution is heated to room temperature, stirred for two hours and then the resulting solid is separated by centrifugation. The solvent is then removed under a high vacuum and the resulting raw product is distilled under a high vacuum (0.0001 kPa (0.001 mbar)). The resulting compound is tBu$_2$Sb—NHtBu (2.56 g, 51% yield) at 36° C. as a colorless liquid.

$^1$H-NMR: (300 MHz, C$_6$D$_6$): δ=1.09 (bs, NH, 1H); 1.21 (s, Sb(C(CH$_3$)$_3$)$_2$, 18H); 1.23 (s, NC(CH$_3$)$_3$, 9H) ppm.
$^{13}$C{$^1$H}-NMR: (75 MHz, C$_6$D$_6$): δ=29.97 (s, SbC(CH$_3$)$_3$); 31.53 (s, SbC(CH$_3$)$_3$); 35.10 (s, NC(CH$_3$)$_3$); 50.94 (s, NC(CH$_3$)$_3$) ppm.
$^{15}$N{$^1$H}-NMR: (51 MHz, C$_6$D$_6$): δ=53.47 (s) ppm.

Example 6: Preparation of tBu$_2$Sb—PHtBu 1.55 g tBu$_2$SbCl (5.71 mmol) is suspended in 50 ml n-pentane. 0.55 g tBuPHLi (5.71 mmol) are added at −20° C., which creates a yellow solution that is stirred overnight. The solids are separated by centrifugation, and the solvent removed under a high vacuum. The result is 1.62 g of the compound tBu$_2$Sb—PHtBu (yield 87%) as a yellow oil.

$^1$H-NMR: (300 MHz, C$_6$D$_6$): δ=1.32 (s, Sb(C(CH$_3$)$_3$)$_2$, 18H); 1.41 (s, PC(CH$_3$)$_3$, 9H); 3.17 (d, $^1J_{PH}$=178 Hz, PH, 1H) ppm.

$^{13}$C{$^1$H}-NMR: (125 MHz, C$_6$D$_6$): δ=29.42 (d, $^2J_{CP}$=2.37 Hz, Sb(C(CH$_3$)$_3$)$_2$); 32.42
(d, $^2$Jcp=4.60 Hz, PC(CH$_3$)$_3$); 34.03 (d, $^1J_{CP}$=12.03 Hz, PC(CH$_3$)$_3$); 35.00 (s, Sb(C(CH$_3$)$_3$)$_2$) ppm.

$^{31}$P{$^1$H}-NMR: (101 MHz, C$_6$D$_6$): δ=−59.62 (s, PH) ppm.

$^{31}$P-NMR: (101 MHz, C$_6$D$_6$): δ=−59.62 (d, $^1J_{HH}$=178 Hz, PH) ppm.

Example 7: Preparation of tBu$_2$Sb—NHiPr 6.20 g tBu$_2$SbCl (22.84 mmol) is dissolved in 40 ml n-pentane, with the former being added drop by drop to a suspension of 1.49 g iPrNHLi (22.84 mmol) in 50 ml n-pentane at −20° C. After stirring overnight, the solid is separated by centrifugation and the solvent removed under a high vacuum. The subsequent distillation at 2 mm Hg at 68° C. results in 3.78 g (yield 56%) of the compound tBu$_2$Sb—HiPr as a colorless liquid.

$^1$H-NMR: (300 MHz, C$_6$D$_6$): δ=0.85 (bs, NH, 1H); 1.15 (d, $^3J_{HH}$=6.28 Hz, NCH(CH$_3$)$_2$, 6H); 1.21 (s, Sb(C(CH$_3$)$_3$)$_2$, 18H); 3.26 (oct, $^3J_{HH}$=6.28 Hz, NCH(CH$_3$)$_2$, 1H) ppm.

$^{13}$C{$^1$H}-NMR: (75 MHz, C$_6$D$_6$): δ=28.57 (s, NCH (CH$_3$)$_2$); 29.91 (s, Sb(C(CH$_3$)$_3$)$_2$); 32.05 (s, Sb(C(CH$_3$)$_3$)$_2$); 49.66 (s, NCH(CH$_3$)$_2$) ppm.

$^{15}$N-NMR: (51 MHz, C$_6$D$_6$): δ=39.41 (s, NH) ppm.

Example 8: Preparation of HP(AstBu$_2$)$_2$ 2.20 g tBu$_2$AsCl (9.8 mmol) in approx. 10 ml THF are added drop by drop to a suspension of 1.72 g [Li(dme)PH$_2$] (9.8 mmol) in approx. 150 ml THF at −60° C. over a period of 15 minutes. The suspension is stirred overnight. The solvent is removed from the clear orange solution, and the residue is accepted in 100 ml n-pentane and filtered. The volume of the solution is then reduced to 10 ml. The compound HP(AstBu$_2$)$_2$ crystallizes from this solution in the form of yellow needles with a yield of 75% (1.50 g).

$^1$H-NMR: (300 MHz, C$_6$D$_6$): δ=1.31 (s, 18H, CH$_3$), 1.35 (d, $^4J_{P,H}$=0.6 Hz, 18H, CH$_3$), 2.72 (d, $^1J_{P,H}$=169.5 Hz, 1H, PH) ppm.

$^{13}$C{1H}-NMR (75 MHz, C$_6$D$_6$): δ=31.2 (d, $^3J_{P,H}$=1.0 Hz, CH$_3$), 31.4 (d, $^3J_{P,H}$=6.5 Hz, CH$_3$), 34.5 (s, C$_{quaternary}$), 36.0 (s, C$_{quaternary}$) ppm $^{31}$P-NMR (121 MHz, C$_6$D$_6$): δ=−150.3 (d, $^1J_{P,H}$=169.6 Hz, PH) ppm.

Example 9: Preparation of HN(SbtBu$_2$)$_2$ 1 ml (1.41 g, 5.19 mmol) tBu$_2$SbCl is presented in 100 ml Et$_2$O at 0 C and then NH$_3$ gas is introduced. This results in spontaneous clouding. After 1.5 hours the reaction comes to an end and the white solid is filtered off. The solvent is removed under a high vacuum, leaving a colorless oil that solidifies into colorless, plate-shaped crystals after some time.

$^1$H-NMR (300 MHz, C$_6$D$_6$): δ=1.30 (s, 36H, C(CH$_3$)$_3$)
$^{13}$C{$^1$H}-NMR (75 MHz, C$_6$D$_6$): δ=29.1 (s, C(CH$_3$)$_3$), 38.7 (s, C(CH$_3$)$_3$) ppm.

Example 10: Preparation of tBu$_2$P—PHtBu 3.79 g (0.022 mol) of tBu$_2$PCl were dissolved in 75 mL of pentane and cooled to −40° C. 2.50 g (0.026 mol) tBuPHLi were added, resulting in yellow coloration of the reaction mixture. A clear liquid was obtained by filtration and removal of the solvent in vacuum. Distillation in vacuum (10$^{-3}$ mbar, 100° C.) resulted in 2.60 g (52%) tBu$_2$P—P(H)tBu.

$^{31}$P{$^1$H}-NMR (C$_6$D$_6$): δ=−52.3 (d, $^1J_{PP}$=232.2 Hz, P(H)tBu), 24.7 (d, $^1J_{PP}$=232.2 Hz, tBu$_2$P).

IR v (cm$^{-1}$)=2989.33 (w), 2936.72 (s), 2891.75 (s), 2858.39 (s), 2707.05 (w), 2307.53 (m, P—H), 1469.31 (s), 1458.99 (s) 1386.10 (m), 1360.88 (s), 1260.28 (w), 1172.56 (s), 1025.56 (m), 1014.16 (m), 932.42 (w), 862.72 (w), 809.16 (s), 760.77 (w), 690.99 (w), 584.61 (w), 566.72 (w), 497.30 (w), 461.05 (w), 410.82 (w).

Example 11: Preparation of tBu$_2$P—NH$_2$
(documented in: O. J. Scherer, G. Schieder, Chem. Ber. 1968, 101, 4184-4198)

28.44 g (0.158 mol, 1.00 eq) of tBu$_2$PCl were suspended in 10 mL diethyl ether and ammonia was condensed into the slurry at −50° C. Ammonium chloride precipitated and formed a white, flaky precipitate. The precipitate was removed by filtration and the raw product was distilled at a pressure of 6.66 mbar and an oil bath temperature of 60° C. 22.8 g (93%) of a colourless, liquid have been obtained.

$^1$H-NMR (300 MHz, C$_6$D$_6$): δ=1.04 (d, J=11.1 Hz, 18H, CH$_3$).

$^{13}$C-NMR 75 MHz, C$_6$D$_6$): δ=28.1 (d, J=15.3 Hz, CH$_3$), 32.9 (d, J=21.5 Hz, C$_{quaternary}$)

$^{31}$P{$^1$H}-NMR (C$_6$D$_6$): δ=62.72 (s, tBu$_2$P—NH2).

$^{31}$P-NMR (C$_6$D$_6$): δ=62.72 (s, tBu$_2$P—NH2).

IR v (cm$^{-1}$)=3457.64 (w, N—H), 3307.77 (w, N—H), 2937.67 (m), 2893.19 (m), 2860.45 (m), 1559.70 (m), 1470.63 (s), 1384.73 (m). 1361.39 (s), 1260.52 (vw), 1189.44 (br, m), 1176.09 (br, m), 1017.29 (m), 956.99 (br, w), 930.69 (w), 806.78 (vs), 602.42 (s), 568.16 (w), 466.37 (m), 442.38 (m).

Deposition of Ga(As$_{1-x}$N$_x$) on GaAs using tBuzAs—NH$_2$ as a nitrogen source.

tBu$_2$As—NH$_2$ (DTBAA=Di-tertbutyl amino arsane), which is intended according to the invention as an educt in a vapor deposition process, has been successfully used as a nitrogen source for the synthesis of gallium arsenide nitride layers (Ga(As$_{1-x}$N$_x$)) (0<x<1) in a MOVPE process, namely for the precipitation of the 13/15 semiconductor Ga(As$_{1-x}$N$_x$) (0<X<1) on gallium arsenide (GaAs) as the substrate.

A commercial system from the manufacturer AIXTRON AG was used for the precipitation (system type: AIX 200 GFR). The precipitation took place with a hydrogen carrier gas flow at a reactor pressure of 5 kPa (50 mbar). Tri-ethyl gallium (Et$_3$Ga) was introduced into the reactor as the gallium source at a pressure of 0.815×10$^{-3}$ kPa (8.15×10$^{-3}$ mbar. The arsenic source used was either the arsenic compound tBuAsH$_2$ (TBAs=tert-butylarsine) (at a pressure of 0.815×10$^{-3}$ kPa (8.15×10$^{-3}$ mbar) in addition to DTBAA, or no additional arsenic source was used. Precipitation of the Ga(As$_{1-x}$N$_x$) layers (0<x<1) occurred at a process temperature of 525° C.

In a first experiment, the representation of Ga(As$_{1-x}$N$_x$) (0<x<1) occurred starting from tri-ethyl gallium (Et$_3$Ga) as the group 13 element source and the single source precursor DTBAA, to be used according to the invention, that served as a source of both nitrogen and arsenic.

In a second experiment, tBuAsH$_2$ (TBAs=tert-butylarsine) was used as an arsenic source in addition to DTBAA.

The characterization of the Ga(As$_{1-x}$N$_x$) layers (0<x<1) was firstly obtained by X-ray diffraction (XRD), and secondly by photoluminescence spectroscopy. A commercially available diffractometer by Panalytical (Panalytical XPert Pro) was used in the X-ray diffraction. ω-2θ measurements were conducted in a high-resolution Eulerian cradle. X-rays were made around the (004) GaAs peak. The recording of the photoluminescence spectra was conducted with the 514 nm line of a cw-Ar ion laser (Coherent Inc) used for excitation. Room temperature photoluminescence was detected with a 1 m grating monochromator (THR 1000, Jobin-Yvon) and a cooled Ge detector using standard lock-in technology.

Figure 1:
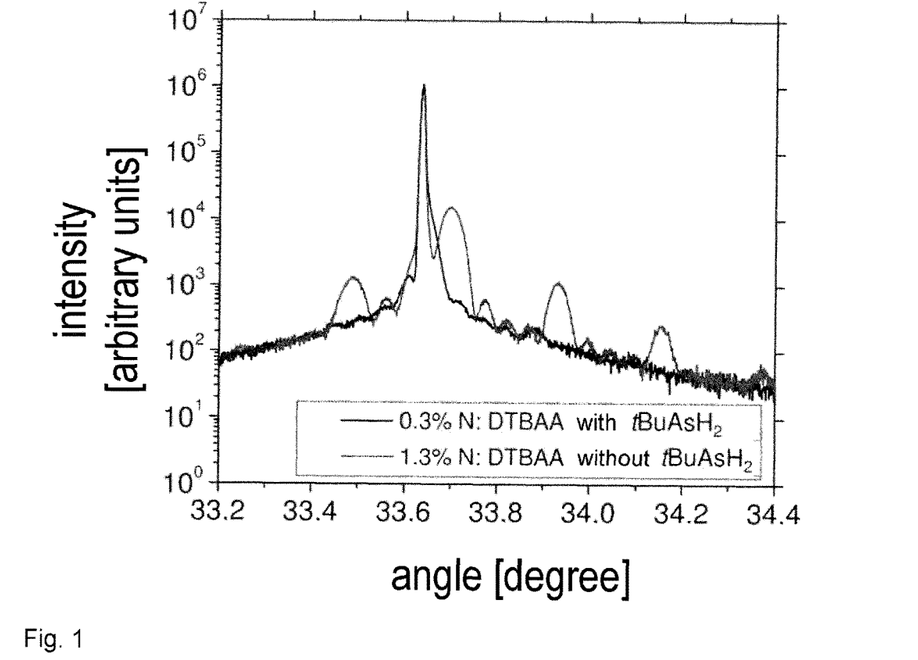
FIG. 1 High-resolution X-ray diffraction profiles of Ga(As$_{1-x}$N$_x$)/GaAs multiple quantum well structures produced using DTBAA (red graph) and/or using DTBAA and TBAs (black graph) and FIG. 2 Photoluminescence spectra of Ga(As$_{1-x}$N$_x$)/GaAs multiple quantum well structures produced using DTBAA (red graph) and/or using DTBAA and TBAs (black graph).
Figure 2:
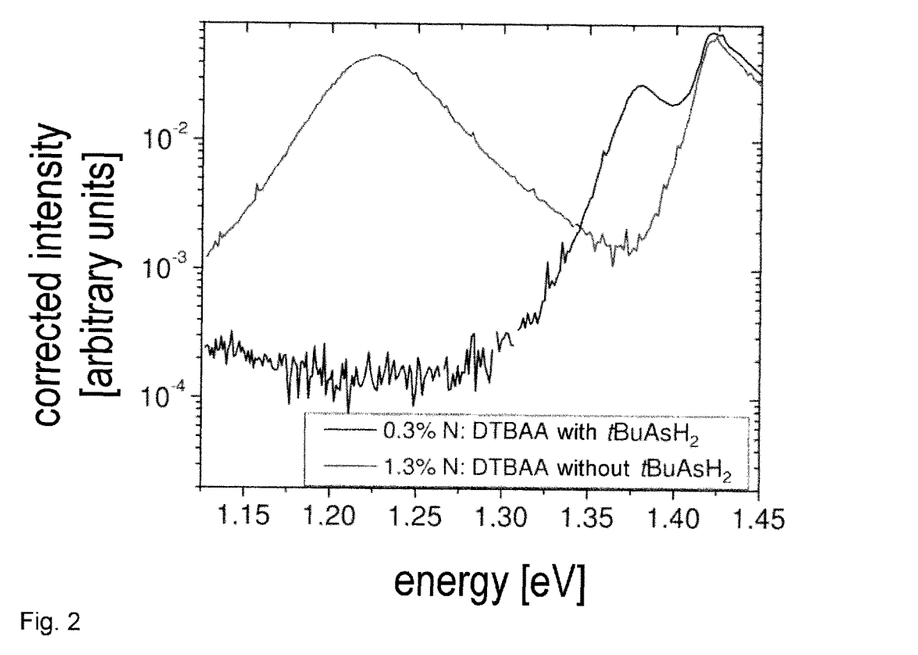

The results of the X-ray diffraction experiments as well as the analyses by photoluminescence spectroscopy are graphically depicted in FIG. 1 and FIG. 2 respectively.

FIG. 1 shows high-resolution X-ray diffraction profiles of Ga(As$_{1-x}$N$_x$)/GaAs multiple quantum well structures with 0<x<1. The red color indicates the high-resolution X-ray diffraction profile of the Ga(As$_{1-x}$N$_x$)/GaAs multiple quantum well structure that was generated by the exclusive use of the binary group 15 element compound DTBAA as provided according to the invention as the arsenic and nitrogen source. The black color indicates the high-resolution X-ray diffraction profile of the Ga(As$_{1-x}$N$_x$)/GaAs multiple quantum well structure that was generated by using DTBAA with TBAs additions.

While the first experiment resulted in a nitrogen content of 1.3% (see FIGS. 1 and 2, red graphs respectively) when only DTBAA was used as a group 15 element precursor, the second experiment saw the inclusion of only 0.3% nitrogen. The nitrogen contents given were determined by dynamic simulations of the X-ray diffraction profiles.

By variation of the process parameters such as, for example, process pressure and temperature, it is possible to also generate higher levels of nitrogen content when only DTBAA is used as the group 15 element precursor.

The values determined from the high-resolution X-ray diffraction profiles (see FIG. 1) for the respective nitrogen content of the two Ga(As$_{1-x}$N$_x$)/GaAs multiple quantum well structures analyzed in two independent experiments (see above: first and second experiment) are confirmed by the results from photoluminescence spectroscopy (see FIG. 2), with 0<x<1.

FIG. 2 shows photoluminescence spectra of the Ga(As$_{1-x}$N$_x$)/GaAs multiple quantum well structures from the first and second experiments. The red color indicates the photoluminescence spectrum of the Ga(As$_{1-x}$N$_x$)/GaAs multiple quantum well structure that was generated by the exclusive use of the binary group 15 element compounds DTBM as provided according to the invention as the arsenic and nitrogen source. The black color indicates in comparison the high-resolution photoluminescence spectrum of the Ga(As$_{1-x}$N$_x$)/GaAs multiple quantum well structure that was generated by using DTBAA with TBA additions.

The two peaks in the red and black graphs of FIG. 2 that are both at low energy values can be attributed to the nitrogenous quantum well (red graph: approx. 1.225 eV; black graph: approx. 1.375 eV). The peak at approx. 1.425 eV derives from the GaAs substrate used. The inclusion of nitrogen into the GaAs structure and thus the generation of Ga(As$_{1-x}$N$_x$) (0<x<1) can be clearly recognized in the case of both experiments by the additional, red-shifted emission—compared to pure GaAs. The exclusive use of DTBAA as the group 15 element precursor (first experiment) allows the observation of a higher nitrogen inclusion (1.3% N) than when DTBAA is used together with TBAs (second experiment, 0.3% N). In FIG. 2, this can be seen in the fact that the red shift in the case of the red graph is greater than in the black graph compared to the pure substrate GaAs.

The use of the binary group 15 element compound DTBAA and the group 13 element precursor Et$_3$Ga according to the invention in a vapor deposition process, in this case MOVPE, therefore leads to the desired deposition of the 13/15 semiconductor Ga(As$_{1-x}$N$_x$), with 0<X<1. The result with regard to the nitrogen inclusion is better than when a mixture of the two group 15 element precursors DTBM and TBAs is used. This is due to the fact that when a mixture of DTBM and TBAs is used, the nitrogen atoms have to compete with the arsenic atoms resulting from the additional arsenic source TBAs, which leads to the result of an overall lower nitrogen content in the desired 13/15 semiconductor Ga(As$_{1-x}$N$_x$) (0<x<1).

The use according to the invention of the binary group 15 element compound DTBAA in a vapor deposition process, here MOVPE, leads to the representation of a ternary, nitrogenous 13/15 semiconductor. The relation of the group 15 elements that should be included in the 13/15 semiconductor to be produced—in this case nitrogen and arsenic—is mainly determined by the composition of the single source precursor. The nitrogen content of the 13/15 semiconductor Ga(As$_{1-x}$N$_x$) (0<X<1) may be influenced and fine tuned by the specific and controlled addition of one or several other group 15 element sources, either according to the invention or already known—as for example in this case the additional, non-binary arsenic source TBAs. This allows the production of 13/15 semiconductors which—compared to the exclusive use of tBuzAs—NH$_2$ as the source of nitrogen and arsenic—have a lower nitrogen content. This may be attributed to the fact that the nitrogen atoms have to compete with the arsenic atoms from the additional arsenic source. The As/N ratio in the 13/15 semiconductor Ga(As$_{1-x}$N$_x$) (0<x<1) to be produced may therefore, for example, be influenced by the variation of the partial pressures of the binary group 15 element source DTBAA and TBAs in the reactor. As an alternative or supplement, for example, the process temperature may be modified. On the whole, the combination and, subsequently, the opto-electronic characteristics of the 13/15 semiconductor and/or the 13/15 semiconductor layers may be varied and/or fine-tuned to a large degree.

The use of an organically substituted nitrogen compound such as 1.1 di-methylhydrazine as the nitrogen source may be waived completely, which drastically reduces nitrogen contaminations—compared to the 13/15 semiconductors and/or 13/15 semiconductor layers produced with the known production methods. Should carbon contaminations possibly be contained in the 13/15 semiconductors and/or 13/15 semiconductor layers that are produced, they usually derive from the group 13 element source or sources that are usually organically substituted. On the whole, the use of the binary group 15 element compound DTBAA according to the invention—without the addition of an organically substituted nitrogen compound as the nitrogen source—allows the production of a defined, ultrapure Ga(As$_{1-x}$N$_x$) layer (0<x<1) with selectable opto-electronic characteristics.

The invention is not limited to one of the embodiments described above, but may be modified in many ways.

Any characteristics and advantages resulting from the claims, the description and the illustrations, including constructive details, spatial arrangement and process steps may be relevant to the invention either separately or in any different combination.

The invention claimed is:

1. A metal-organic chemical vapor deposition process for introducing
a 13/15 semiconductor layer, comprising
exposing a surface, under conditions suitable for deposition, to at least one binary group 15 element compound as the educt, as to form a 13/15 semiconductor layer on the surface,
wherein the at least one binary group 15 element compound has the general formula $$R^1R^2E\text{-}E'R^3R^4 \qquad (I),$$

wherein
R$^1$, R$^2$, R$^3$ and R$^4$ are selected independently from one another from the group consisting of H, an alkyl radical (C1-C10) and an aryl group, and
E and E' are selected independently from one another from the group consisting of N, P, As, Sb and Bi,
wherein E=E' or E≠E', and
wherein hydrazine and its derivatives are excluded from the usage indicated, and/or
wherein at least one binary group 15 element compound has the general formula $$R^5E(E'R^6R^7)_2 \qquad (II),$$

wherein
R$^5$, R$^6$ and R$^7$ are selected independently from one another from the group consisting of H, an alkyl radical (C1-C10) and an aryl group, and
E and E' are selected independently from one another from the group consisting of N, P, As, Sb and Bi,
wherein E=E' or E≠E'.

2. The process according to claim 1, wherein the educt is a binary group 15 element compound of the general formula (I) and
R$^1$ and R$^2$ are selected independently from one another from the group consisting of an alkyl radical (C1-C10) and an aryl group, and
R$^3$=R$^4$=H.

3. The process according to claim 2, wherein the binary group 15 element compound of the general formula (I) is selected from the group consisting of tBu$_2$P—NH$_2$, (CF$_3$)$_2$P—NH$_2$, Ph$_2$P—NH$_2$, tBu$_2$P—AsH$_2$, tBu$_2$As—NH$_2$, tBu$_2$As—PH$_2$, Ph$_2$As—PH$_2$, tBu$_2$Sb—NH$_2$ and tBu$_2$Sb—PH$_2$.

4. The process according to claim 1, wherein the educt is a binary group 15 element compound of the general formula (I) and
R$^1$, R$^2$ and R$^4$ are selected independently from one another from the group consisting of an alkyl radical (C1-C10) and an aryl group, and
R$^3$=H.

5. The process according to claim 4, wherein the binary group 15 element compound of the general formula (I) is selected from the group consisting of tBu$_2$As—PHMe, tBu$_2$Sb-NHtBu, tBu$_2$Sb-PHtBu and tBu$_2$Sb-NHtPr.

6. The process according to claim 1, wherein the educt is a binary group 15 element compound wherein the general formula (I), and R$^1$, R$^2$, R$^3$ and R$^4$ are independently selected from each other from the group consisting of an alkyl radical (C1-C10) and an aryl group.

7. The process according to claim 6, wherein the binary group 15 element compound of the general formula (I) is selected from the group consisting of Me$_2$As—AsMe$_2$, tBu$_2$Sb—NMe$_2$, iPr$_2$Sb—PMe$_2$, Et$_2$Sb—NMe$_2$, Et$_2$Sb—P(CH$_5$)$_2$, tBu$_2$Bi—PtBu$_2$ and tBu$_2$Bi—AstBu$_2$.

8. The process according to claim 1, wherein the educt is a binary group 15 element compound of the general formula (II) and
R$^5$=H.

9. The process according to claim 8, wherein the binary group 15 element compound of the general formula (II) is selected from the group consisting of HP(AstBu$_2$)$_2$ and HN(SbtBu$_2$)$_2$.

10. The process according to claim 1, wherein the educt is a binary group 15 element compound of the general formula (II) and
R$^5$ is selected from the group consisting of an alkyl radical (C1-C10) and an aryl group, and
R$^6$=R$^7$=H.

11. The process according to claim 10, wherein the binary group 15 element compound of the general formula (II) is selected from the group consisting of tBuP(NH$_2$)$_2$, tBuAs(NH$_2$)$_2$ and (C$_6$H$_5$)P(NH$_2$)$_2$.

12. The process according to claim 1, wherein the educt is a binary group 15 element compound of the general formula (II) and
R$^5$ and R$^7$ are selected independently from one another from the group consisting of an alkyl radical (C1-C10) and an aryl group, and
R$^6$=H.

13. The process according to claim 12, wherein the binary group 15 element compound of the general formula (II) is selected from the group consisting of nBuP(AsHMe)$_2$ and (C$_6$H$_5$)P(AsHMe)$_2$.

14. The process according to claim 1, wherein the educt is a binary group 15 element compound of the general formula (II) and
R$^5$, R$^6$, and R$^7$ are selected independently from one another from the group consisting of an alkyl radical (C1-C10) and an aryl group.

15. The process according to claim 14, wherein the binary group 15 element compound of the general formula (II) is selected from the group consisting of tBuAs(NMe$_2$)$_2$, m-F$_3$CC$_6$H$_4$As(NMe$_2$)$_2$ and tBuAs(PMe$_2$)$_2$.

* * * * *